US006939492B2

(12) United States Patent
Jackson et al.

(10) Patent No.: US 6,939,492 B2
(45) Date of Patent: Sep. 6, 2005

(54) METHOD FOR MAKING FIBROUS WEB MATERIALS

(75) Inventors: David Martin Jackson, Roswell, GA (US); Jason Sybren Fairbanks, Gainesville, GA (US); John Gavin MacDonald, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 162 days.

(21) Appl. No.: 10/329,933

(22) Filed: Dec. 26, 2002

(65) Prior Publication Data

US 2004/0155383 A1 Aug. 12, 2004

(51) Int. Cl.[7] .................. A61F 13/15; A61F 13/20; B32B 5/02; D04H 3/16; B29C 59/00
(52) U.S. Cl. .................. 264/116; 442/59; 442/118; 264/121; 264/122; 264/128; 604/358
(58) Field of Search ................. 264/109–128; 604/358; 442/59, 118

(56) References Cited

U.S. PATENT DOCUMENTS

| | | |
|---|---|---|
| 2,544,019 A | 3/1951 | Heritage |
| 3,577,312 A | 5/1971 | Videen et al. |
| 3,950,218 A | 4/1976 | Levesque |
| 3,950,219 A | 4/1976 | Levesque |
| 4,354,487 A | 10/1982 | Oczkowski et al. |
| 4,375,448 A | 3/1983 | Appel et al. |
| 4,376,440 A | 3/1983 | Whitehead et al. |
| 4,488,928 A | 12/1984 | Ali Khan et al. |
| 4,494,278 A | 1/1985 | Kroyer et al. |
| 4,539,996 A | 9/1985 | Engel |
| 4,554,924 A | 11/1985 | Engel |
| 4,640,810 A | 2/1987 | Laursen et al. |
| 4,647,324 A * | 3/1987 | Mtangi et al. ............. 156/62.2 |
| 4,738,867 A | 4/1988 | Itoh et al. |

(Continued)

FOREIGN PATENT DOCUMENTS

| | | |
|---|---|---|
| EP | 0040087 B1 | 9/1984 |
| WO | 01/26592 | 4/2001 |

OTHER PUBLICATIONS

American Society for Testing and Materials (ASTM) Designation: D: 724–89, "Standard Test Method for Surface Wettability of Paper," Jul. 1989, pp. 113–115.

*Primary Examiner*—Stephen J. Lechert, Jr.
(74) *Attorney, Agent, or Firm*—Robert A. Ambrose

(57) ABSTRACT

Disclosed herein is a method for making fibrous web materials which may be used in or as absorbent core materials for absorbent products. The method involves providing loose fibers, entraining the fibers in a moving airstream, treating the fibers with an energy-activatable pre-polymer composition and subjecting the fibers to activation energy to initiate cross-linking of the composition. The fibers are collected on forming surface to form a fibrous web. The fibers may be treated with the composition while entrained in the moving air or after being collected on the forming surface, or in an alternate embodiment by treating with the composition a mat of fibers from which the loose fibers are provided. The fibrous web material may comprise cellulosic fibers such as pulp, and/or synthetic fibers such as staple fibers, and/or super absorbent materials.

22 Claims, 1 Drawing Sheet

U.S. PATENT DOCUMENTS

| | | | |
|---|---|---|---|
| 4,835,020 A | 5/1989 | Itoh et al. | |
| 5,064,689 A | 11/1991 | Young, Sr. et al. | |
| 5,108,820 A | 4/1992 | Kaneko et al. | |
| 5,108,827 A | 4/1992 | Gessner | |
| 5,126,189 A | 6/1992 | Tanny et al. | |
| 5,128,082 A * | 7/1992 | Makoui | 264/112 |
| 5,149,334 A | 9/1992 | Lahrman et al. | |
| 5,188,624 A | 2/1993 | Young, Sr. et al. | |
| 5,328,935 A | 7/1994 | Van Phan et al. | |
| 5,330,822 A | 7/1994 | Berg et al. | |
| 5,336,552 A | 8/1994 | Strack et al. | |
| 5,382,400 A | 1/1995 | Pike et al. | |
| 5,407,717 A | 4/1995 | Lucast et al. | |
| 5,428,076 A | 6/1995 | Roe | |
| 5,432,000 A | 7/1995 | Young, Sr. et al. | |
| 5,451,353 A | 9/1995 | Rezai et al. | |
| 5,498,478 A | 3/1996 | Hansen et al. | |
| 5,506,035 A | 4/1996 | Van Phan et al. | |
| 5,516,585 A | 5/1996 | Young, Sr. et al. | |
| 5,527,171 A | 6/1996 | Soerensen | |
| 5,538,783 A | 7/1996 | Hansen et al. | |
| 5,547,541 A | 8/1996 | Hansen et al. | |
| 5,547,747 A | 8/1996 | Trokhan et al. | |
| 5,549,928 A | 8/1996 | Trokhan et al. | |
| 5,571,618 A | 11/1996 | Hansen et al. | |
| 5,578,369 A | 11/1996 | Nohr et al. | |
| 5,589,256 A | 12/1996 | Hansen et al. | |
| 5,607,759 A | 3/1997 | Hansen et al. | |
| 5,609,727 A | 3/1997 | Hansen et al. | |
| 5,611,885 A | 3/1997 | Hansen et al. | |
| 5,614,570 A | 3/1997 | Hansen et al. | |
| 5,641,561 A | 6/1997 | Hansen et al. | |
| 5,693,411 A | 12/1997 | Hansen et al. | |
| 5,709,955 A | 1/1998 | Nohr et al. | |
| 5,713,881 A | 2/1998 | Rezai et al. | |
| 5,722,482 A | 3/1998 | Buckley | |
| 5,789,326 A | 8/1998 | Hansen et al. | |
| 5,797,893 A | 8/1998 | Wada et al. | |
| 5,800,418 A | 9/1998 | Ahr | |
| 5,851,672 A | 12/1998 | Wang et al. | |
| 5,859,077 A | 1/1999 | Reichman et al. | |
| 5,910,224 A | 6/1999 | Morman | |
| 5,955,023 A | 9/1999 | Ioffe et al. | |
| 5,977,014 A | 11/1999 | Plischke et al. | |
| 5,985,432 A | 11/1999 | Wang et al. | |
| 5,998,032 A | 12/1999 | Hansen et al. | |
| 6,022,610 A | 2/2000 | Phan et al. | |
| 6,071,549 A | 6/2000 | Hansen | |
| H1909 H | 11/2000 | Ahr | |
| 6,150,582 A | 11/2000 | Wada et al. | |
| 6,187,872 B1 | 2/2001 | Yanase et al. | |
| 6,229,062 B1 | 5/2001 | Mandell et al. | |
| 6,261,679 B1 | 7/2001 | Chen et al. | |
| 6,270,893 B1 | 8/2001 | Young, Sr. et al. | |
| 6,310,113 B1 | 10/2001 | Reichman et al. | |
| 6,312,484 B1 | 11/2001 | Chou et al. | |
| 6,319,599 B1 | 11/2001 | Buckley | |
| 6,368,533 B1 | 4/2002 | Morman | |

\* cited by examiner

METHOD FOR MAKING FIBROUS WEB MATERIALS

TECHNICAL FIELD

This invention relates to fibrous web materials and liquid absorbent fibrous web materials and a method for making the same.

BACKGROUND OF THE INVENTION

Disposable absorbent products such as mortuary, veterinary and personal care absorbent products such as diapers, feminine pads, adult incontinence products, and training pants often include one or more layers of fibrous web materials, especially liquid absorbent fibrous web materials, as an absorbent core material, and a backing layer or moisture barrier layer which is impervious to fluid. Personal care absorbent products typically also include a surface for contacting the body of the user, and the absorbent fibrous web material is generally disposed between the body-contacting surface and the moisture barrier layer so that body fluids are absorbed into the product and are contained by the moisture barrier.

Such absorbent fibrous web materials are frequently formed as nonwoven fibrous webs, such as for example, a pulp fluff/super absorbent composite structure which may also contain longer synthetic staple fibers. In order to maintain proper structural integrity when utilized as, or as part of, an absorbent core material, it is necessary to bond or otherwise stabilize the structure of the fibrous web material. Methods are known in the art for providing structural integrity to absorbent fibrous web material such as by thermal pattern or point bonding by the application of heat and pressure, or through-air bonding with heated air. However, heat bonding techniques such as point bonding and through-air bonding generally require the presence of a meltable web component such as thermoplastic bicomponent staple fibers, the presence of which will not always be desirable for all end-use applications. In addition, thermal bonding is relatively inefficient, uses large amounts of energy and the long heating time required uses large amounts of process space. Thus, there remain continuing opportunities for improved methods for making fibrous webs and absorbent fibrous web materials.

SUMMARY OF THE INVENTION

The present invention provides a method for making a fibrous web material including the steps of providing a plurality of loose fibers, entraining the loose fibers in a stream of moving air, treating the fibers with an energy-activatable pre-polymer composition, subjecting the treated fibers to activation energy to initiate a cross-linking reaction in the energy-activatable pre-polymer composition, and collecting the fibers on a moving forming surface to form a fibrous web. Treating the fibers may comprise spraying the energy-activatable pre-polymer composition into the stream of moving air while the fibers are therein entrained or may comprise spraying the composition onto the fibrous web after the fibers are collected on the forming surface. The loose fibers may desirably comprise cellulosic fibers such as wood pulp fibers, and the fibrous web material may desirably further comprise super absorbent materials and/or synthetic fibers. The method may further comprise the step of compacting the web and the cross-linking reaction may desirably come to completion or substantial completion either before or after compacting the web. The energy-activatable pre-polymer composition may desirably comprise an epoxy resin and photoinitiator, and may further comprise hydrophilic treatments. Fibrous web materials made by the method of the invention are useful as or as part of absorbent core materials in personal care absorbent products and in other absorbent products.

In another embodiment, the method for making the fibrous web includes providing a mat of fibers, treating the mat of fibers with an energy-activatable pre-polymer composition, forming a plurality of loose fibers from the treated mat of fibers, entraining the loose fibers in a stream of moving air, subjecting the fibers to activation energy to initiate a cross-linking reaction in the energy activatable pre-polymer composition, and collecting the fibers on a moving forming surface to form a fibrous web. The treated mat of fibers may be a cellulosic fiber mat or a synthetic fiber mat.

DEFINITIONS

Figure 1:
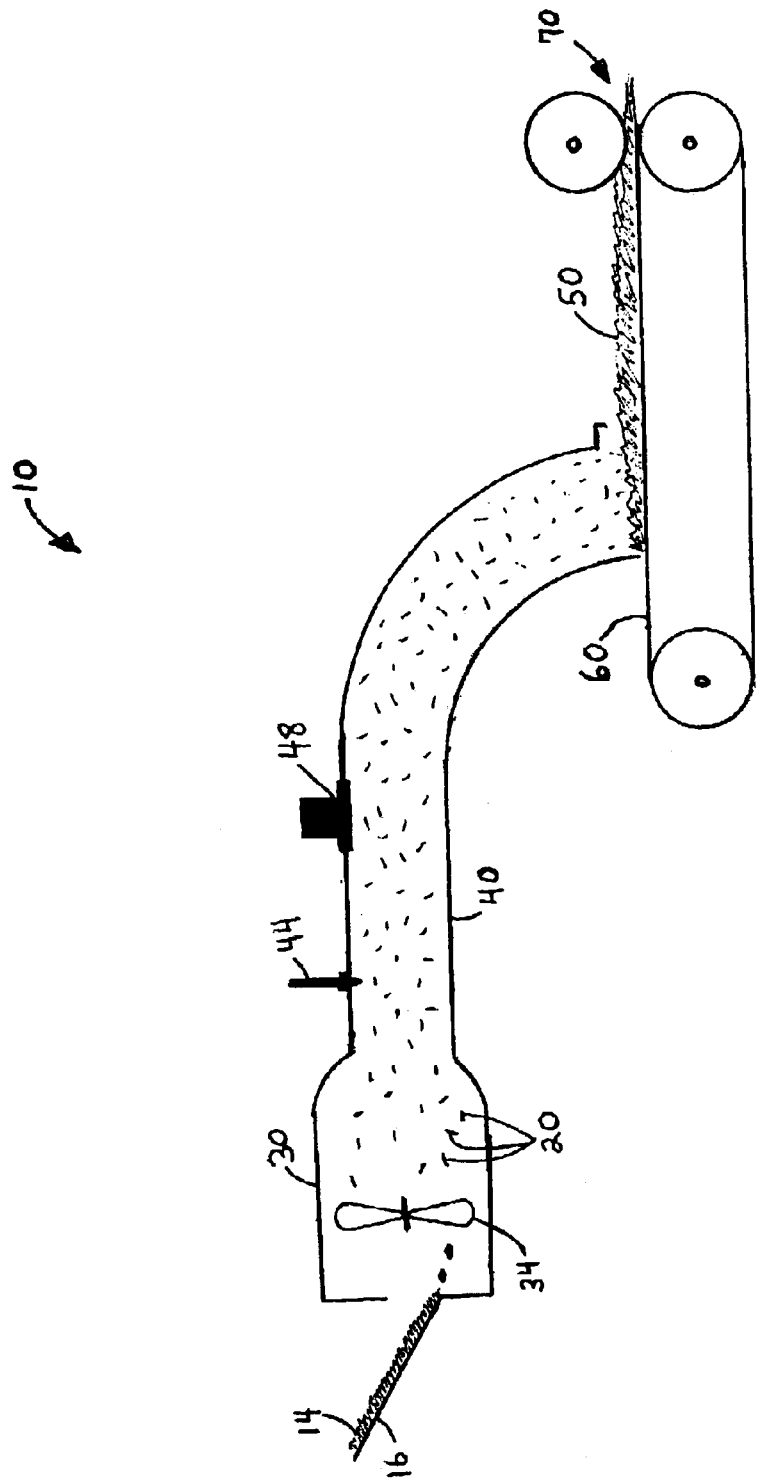
FIG. 1 is a schematic illustration of an exemplary process line for making fibrous webs in accordance with the invention.

As used herein and in the claims, the term "comprising" is inclusive or open-ended and does not exclude additional unrecited elements, compositional components, or method steps.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and random symmetries.

As used herein the term "monocomponent" fiber refers to a fiber formed from one or more extruders using only one polymer extrudate. This is not meant to exclude fibers formed from one polymer to which small amounts of additives have been added for color, anti-static properties, lubrication, hydrophilicity, etc. These additives, e.g. titanium dioxide for color, are generally present in an amount less than 5 weight percent and more typically about 2 weight percent.

As used herein the term "conjugate fibers" refers to fibers which have been formed from at least two polymers, or the same polymer with different properties, extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios.

As used herein the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner.

As used herein the term "nonwoven fibrous web" means a web having a structure of individual fibers or filaments which are interlaid, but not in an identifiable manner as in a knitted or woven fabric. Nonwoven fabrics or webs have been formed from many processes such as for example, meltblowing processes, spunbonding processes, and dry-forming techniques such as carding and air-laying processes. The basis weight of nonwoven fabrics is usually expressed in grams per square meter (gsm) or ounces of material per square yard (osy) and the fiber diameters useful are usually expressed in microns. (Note that to convert from osy to gsm, multiply osy by 33.91.)

As used herein the term "staple fiber webs" refers to dry-formed nonwoven webs of staple fibers such as those made by carding or air-laying processes. Briefly, the air forming or air-laying process is a well known process by which a fibrous nonwoven web can be formed. In the air-laying process, bundles of small fibers having typical lengths ranging from about 3 to about 50 millimeters (mm) are separated and entrained in an air supply or air stream and then deposited onto a forming screen or other foraminous forming surface, usually with the assistance of a vacuum supply, in order to form a dry-laid fiber web. Equipment for producing air-laid webs includes the Rando-Weber air-former machine available from Rando Corporation of New York and the Dan-Web rotary screen air-former machine available from Dan-Web Forming of Risskov, Denmark.

As used herein "carded webs" refers to nonwoven webs formed by carding processes as are known to those skilled in the art and further described, for example, in U.S. Pat. No. 4,488,928 to Alikhan and Schmidt which is incorporated herein in its entirety by reference. Briefly, carding processes involve starting with staple fibers in a bulky batt that is combed or otherwise treated to provide a web of generally uniform basis weight.

As used herein, an "airlaid" web is a fibrous web structure formed primarily by a process involving deposition of loose, air-entrained fibers onto a porous forming surface. Generally the web comprises cellulosic fibers such as those from fluff pulp that have been separated from a mat of fibers, such as by a hammermilling process, and then entrained in a moving stream of air and deposited or collected on the porous forming surface. There may also be longer fibers such as synthetic staple fibers or binder fibers present, and typically following collection of the fibers on the forming surface the web is densified and/or bonded by such means as thermal bonding or adhesive bonding. Further, an airlaid web to which binder material is subsequently added can be considered within the scope of the term "airlaid" according to the present invention. In addition, super absorbent materials in particulate of fiber form may be included in airlaid webs where desired.

As used herein, the term "cellulosic" is meant to include materials having cellulose as a major constituent, and specifically comprising at least 50 percent by weight cellulose or a cellulose derivative. Therefore the term cellulosic includes, without limitation, cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose.

As used herein, the term "hydrophilic" with regard to polymeric or cellulosic material means that the material has a surface free energy such that the material is wettable by an aqueous medium, i.e. a liquid medium of which water is a major component. The hydrophilicity of materials can be measured, for example, in accordance with the ASTM-D-724-89 contact angle testing procedure. For example, a hydrophilic polymeric material has an initial contact angle equal to or less than about 90°. Depending on material application needs and degree of hydrophilicity desired, this term includes materials where the initial contact angle may desirably be equal to or less than about 75°, or even equal to or less than about 50°. The term "initial contact angle" as used herein indicates a contact angle measurement made within about 5 seconds of the application of water drops on a test film specimen. The term "hydrophobic" includes those materials that are not hydrophilic as defined. It will be recognized that hydrophobic materials may be treated internally or externally with surfactants and the like to render them hydrophilic, and that slightly or moderately hydrophilic materials may be treated to make them more hydrophilic.

DESCRIPTION OF THE INVENTION

The present invention is directed to methods for making fibrous web materials. The invention will be described with reference to certain embodiments and with reference to an illustrated process line in FIG. 1. It will be apparent to those skilled in the art that these embodiments do not represent the full scope of the invention which is broadly- applicable in the form of variations and equivalents as may be embraced by the claims appended hereto. It is intended that the scope of the claims extend to all such variations and equivalents.

In one embodiment of the invention, the method of making the fibrous web material comprises providing loose fibers and entraining the loose fibers in a moving airstream wherein the fibers are treated with an energy-activatable pre-polymer composition, the treated fibers are subjected to an activation energy source which initiates a cross-linking reaction in the energy-activatable pre-polymer composition, and the fibers are collected on a moving forming surface to form a fibrous web material. The fibrous web forming method may utilize conventional air-laying processes as are known in the art, such as is disclosed for example in U.S. Pat. No. 4,640,810 to Laursen et al., U.S. Pat. No. 4,494,278 to Kroyer et al., U.S. Pat. No. 5,527,171 to Soerensen and U.S. Pat. No. 4,375,448 to Appel et al., or may utilize the air-forming process used to produce the absorbent core material in personal care absorbent products such as diapers, in situ on the product converting machine, conventionally referred to as a fluff end of the converting or product forming process.

As shown in the exemplary process line 10 in FIG. 1, mat of fibers 14 is fed down fiber chute 16 into air-laying apparatus 30. Fan 34 draws in clumps of fibers from fibrous mat 14 and then acts to individualize the fibers into loose fibers 20 and entrain the loose fibers 20 in a moving airstream. The loose fibers 20 are then conducted along duct 40, until being collected as fibrous web material 50 upon the forming surface 60. While fibers 20 are entrained in the stream of moving air, the fibers 20 are treated with the energy-activatable pre-polymer composition by spraying the composition into the moving airstream at spray nozzle 44. The energy-activatable pre-polymer composition may be sprayed into the moving airstream by conventional spray nozzles as are known in the art, such as by one or more atomization spray nozzles such as are available from Spraying Systems Company of Wheaton, Ill., for example. Generally speaking, the energy-activatable pre-polymer composition will be applied in an amount which is from about 0.5 weight percent to about 30 weight percent, based on the basis weight of the fibrous web material produced. Desirably, the energy-activatable pre-polymer composition will be applied at about 0.5 to about 8 weight percent, and for many applications it will be desirable that the loose fibers obtain only a thin coating of the treatment composition and that the fibrous web material comprise about 1 to about 3 percent of the composition. After being treated with the energy-activatable pre-polymer composition and while still in the moving airstream, the treated fibers are subjected to the activation energy via port 48 in order to start or initiate a cross-linking reaction in the pre-polymer composition, and the fibers are then delivered via the moving airstream to forming surface 60 as stated above where they are deposited in the form of fibrous web material 50. The fibrous web material may desirably be compacted or densified at nip 70. As the energy-activatable pre-polymer composition cross-links it cures into a polymer which acts as an aid in binding the loose fibers together and thereby stabilizing the web, that is, providing integrity to the structure of the fibrous web material 50. Fibrous web material 50 may desirably range in basis weight from about 50 grams per square meter (gsm) or less up to about 1000 gsm, or higher.

The loose fibers may desirably be pulp fibers or other absorbent cellulosic fibers as are known in the art. Additional components may be added to the fibrous web material by entraining the additional components into the moving airstream with the loose fibers, either before or after the loose fibers are treated with the energy-activatable pre-polymer composition. Desirably, the additional components may be added by combining the cellulosic fibers and the additional components upstream of the fan and entraining all of the components in the airstream. As a specific example, where the fibrous web material will be used as an absorbent component in a personal care absorbent product such as a diaper or incontinence garment or a feminine care pad, one or more super absorbent materials as are known in the art may desirably be entrained in the airstream, in the form of super absorbent particles or super absorbent fibers, along with the loose pulp or cellulosic fibers. As another example, where it is desired for the fibrous web material to have additional structural integrity, about 2 to about 10 percent by weight and up to about 20 percent by weight of longer fibers such as synthetic staple-length fibers may be incorporated in the fibrous web material. These longer fibers may be incorporated in the fibrous web material by entraining them in the moving airstream with the loose fibers, either before or after spraying the energy-activatable pre-polymer composition into the airstream. The addition of longer fibers acts to increase structural integrity by "tying" the fibrous web material together, because the longer fibers run for a greater extent of the fibrous web material than do the shorter pulp or other cellulosic fibers. Examples of useful synthetic fibers include thermoplastic staple fibers such as polyester, polyolefin and nylon fibers, and man made cellulosic fibers such as lyocell rayon fibers as are known in the art to be suitable for air-laying processes, and will typically be crimped fibers of about 6 millimeters to about 12 millimeters in length, although somewhat shorter fibers or longer fibers may be utilized.

The energy-activatable pre-polymer composition which is sprayed into the moving airstream to treat the loose fibers may desirably comprise a photoinitiator and an adhesive precursor which, when cross-linked, polymerizes to become an adhesive polymer suitable for binding together the loose fibers, thereby providing structural integrity to the fibrous web material. For such an energy-activatable pre-polymer composition, one may initiate the cross-linking reaction by exposing the energy-activatable pre-polymer composition to a source of activation energy such as ultraviolet radiation provided by an excimer lamp or other commercially available ultraviolet source. Once initiated by exposure to the activation energy, the cross-linking reaction continues even without continued exposure to activation energy. One example of an energy-activatable pre-polymer composition may desirably comprise an aryl sulfonium salt photoinitiator and a cycloaliphatic epoxide resin. Such photoinitiators and epoxide resins are commercially available from The Dow Chemical Company under the trade name CYRACURE. The energy-activatable pre-polymer composition may further comprise a flexibilizer such as a vinyl chloride/vinyl acetate/vinyl alcohol terpolymer as is available from The Dow Chemical Company under the trade name UCAR VAGH. As a specific example of an energy-activatable pre-polymer composition comprising the foregoing, the energy-activatable pre-polymer composition may desirably comprise by weight about 1 percent to about 10 percent triaryl sulfonium salt photoinitiator, about 60 percent to about 94 percent diepoxide resin and about 5 percent to about 30 percent of a vinyl chloride/vinyl acetate/vinyl alcohol terpolymer flexibilizer. Such a composition, and other suitable energy-activatable pre-polymer compositions, are described in U.S. Pat. No. 5,578,369 to Nohr and MacDonald, incorporated herein in its entirety by reference.

It will be noted that other energy-activatable pre-polymer compositions and/or activation energy sources known to one skilled in the art may be usefully employed in the practice of the invention. For example, other epoxy, vinyl ether, acrylate and methacrylate adhesives are known and may be produced by subjecting an energy-activatable pre-polymer composition including commercially available monomers or oligomers and photoinitiators to ultraviolet, electron beam, or other activation energy. For certain energy-activatable pre-polymer compositions such as methacrylic acid, ethyl acrylate, methyl methacrylate, vinyl acrylate and other acrylates, where electron beam is the activation energy source, a photoinitiator is not required. The particular activation energy selected to initiate the cross-linking reaction will depend on the resin and/or photoinitiator selction for the energy-activatable pre-polymer composition. For example, for the aryl sulfonium salt photoinitiator and a cycloaliphatic epoxide resin energy-activatable pre-polymer composition described above, the cross-linking reaction may suitably be initiated by exposure to ultraviolet radiation having a wavelength of about 260 nanometers to about 360 nanometers provided by an excimer lamp. Alternatively, the duct may comprise more than one window so that the activation energy may be provided by multiple sources, or may comprise an entire section which is substantially transparent to the activation energy so that the energy may be beamed into the duct from all sides.

It should be noted that the amount of photoinitiator to be used in the energy-activatable pre-polymer composition will depend on the desired cross-linking reaction kinetics. For example, where the loose fibers are subjected to the activation energy while entrained in the moving airstream, such as by passing through a beam of ultraviolet radiation which is introduced through a port, such as a quartz window, in a wall of the air chamber, it may be desirable for the reaction to come to completion or be substantially complete just after the treated loose fibers have been collected into the fibrous web material on the moving forming surface, so that the loose fibers will be bound together and the fibrous web material will have structural integrity. Alternatively, it may be desirable for the reaction to come to completion or substantially to completion at some later point in the production process. In the first instance, relatively more of the photoinitiator would be used while in the second instance relatively less of the photoinitiator would be used in the energy-activatable pre-polymer composition. As a specific example, it may be desirable to compress or densify the fibrous web material by use of compaction rollers as are known in the art. Where it is desired that the fibrous web material be able to maintain such a densified structure it would be desirable to have the cross-linking reaction come to completion at some point in the process after being collected into the fibrous web material, such as having the reaction complete either just as or just after the fibrous web material undergoes compaction. As another example, it may be desirable to mold the fibrous web material by the application of pressure into a specific shape or to introduce deviation to the flat planar structure of the web, such as by curving the fibrous web material into a body-conforming curved shape, in which case it would be advantageous to have the cross-linking reaction come to completion or be substantially complete at a time proximate to the molding step.

Depending on desired end use for the nonwoven material, it may be beneficial to add other treatments or additives to the web such as for example treatments to impart or increase hydrophilicity, or colorants or pigments. While these additional treatments may be applied to the fibrous web material after it has been formed, it may be advantageous and efficient for them to be added to the energy-activatable pre-polymer composition instead, as long as they do not interfere with the ability of the activation energy to initiate the cross-linking reaction in the energy-activatable pre-polymer composition. Other alternatives are also possible. As an example, the air-forming process described above for the fibrous web material may be incorporated into a larger product-forming process, so that the fibrous web material is formed as an absorbent core material directly in-line in the manufacturing process of a diaper or incontinence garment or feminine care product.

As a specific example, the method of the invention may be practiced as follows. A mat of conventional softwood kraft pulp fibers such as the fibers designated NB416 and commercially available from the Weyerhaeuser Company of Federal Way, Wash. may be fed into a hammermill and fiberized to form the loose cellulosic fibers. The loose cellulosic fibers may then be fed down a feeder chute into an air-laying apparatus where a fan individualizes the fibers and entrains the fibers in an airstream. Then, while the fibers are in the airstream and being conducted along a duct towards the forming surface, the fibers may be treated with an energy-activatable pre-polymer composition by spraying the composition into the duct to coat the fibers at a 5 weight percent rate, that is, an amount of energy-activatable pre-polymer composition sufficient to comprise 5 percent of the weight of the formed fibrous web material. The energy-activatable pre-polymer composition may desirably comprise by weight 80 percent cycloaliphatic epoxide resin, 5 percent triaryl sulfonium salt photoinitiator and 15 percent vinyl chloride/vinyl acetate/vinyl alcohol terpolymer flexibilizer. After being treated with the energy-activatable pre-polymer composition and while the fibers are still entrained in the airstream, the treated fibers may be subjected to ultraviolet activation energy from xenon chloride excimer lamps which emit ultraviolet light energy at a wavelength of 308 nanometers to initiate the cross-linking reaction. The treated fibers may be subjected to the activation energy through quartz glass windows in the duct. Then, the fibers may be collected into a fibrous web material on a moving foraminous forming wire and transported through a pressurized roller nip to compact or densify the web. The formed fibrous web material may then be used as an absorbent core material in a personal care absorbent product.

As another embodiment of the invention, the fibrous web material may be produced in accordance with the embodiments and/or alternatives described above, except for the following difference. Instead of treating all of the loose fibers which are to be incorporated into the fibrous web material by spraying the energy-activatable pre-polymer composition directly into the air-forming chamber of the air-laying apparatus or into the moving airstream, and thereby stabilizing the fibrous web material throughout its entire thickness, only the fibers on one surface of the fibrous web material are treated with the energy-activatable pre-polymer composition. In this embodiment, the loose fibers may be formed on an air-laying process as described above but the energy-activatable pre-polymer composition treatment is not applied until some point after the fibers have been collected on the moving forming surface. After the fibers are collected on the forming surface, the energy-activatable pre-polymer composition is sprayed onto one surface of the formed web and that surface of the web is subjected to activation energy to initiate the cross-linking reaction, thereby causing the fibrous web material to be bonded throughout only a portion of its thickness. That is, the fibrous web material will be bonded only to that depth of its thickness which both the liquid energy-activatable pre-polymer composition and the activation energy are able to penetrate. This embodiment may also suitably be incorporated as a portion of an in-line product manufacturing process for diapers or the like, to form the fibrous web material as an absorbent material which is stabilized primarily on one surface.

In still a further embodiment, the fibrous web material is produced by the steps of providing a mat of fibers, treating the mat of fibers with an energy-activatable pre-polymer composition, forming a plurality of loose fibers from the treated mat of fibers, entraining the loose fibers in a moving airstream, subjecting the fibers to an activation energy to initiate the cross-linking reaction, and collecting the fibers on a moving forming surface to form the fibrous web material. The mat of fibers supplied may be a mat of synthetic fibers which is dipped into a bath of energy-activatable pre-polymer composition or onto which the energy-activatable pre-polymer composition is sprayed. The fibrous web material may then be wholly composed of the synthetic fibers, or may further comprise super absorbent materials which are added by entraining in the stream of moving air as described in the embodiments above. Alternatively, the fibrous web material may further comprise pulp or other cellulosic fibers added by entraining the pulp fibers in the stream of moving air. In this case, the fibrous web material would be comprised of the longer synthetic fibers which have been treated with the energy-activatable pre-polymer composition and the shorter pulp or cellulosic fibers which have not been treated with the energy-activatable pre-polymer composition, such that the longer fibers become the "skeleton" running throughout the fibrous web material which stabilizes or lends structural integrity to the fibrous web material. The treated fibers may be subjected to activation energy either while entrained in the moving airstream or after being collected upon the moving forming surface, as was described above.

As still another alternative, the mat of fibers which is treated with the energy-activatable pre-polymer composition may be a mat of pulp fibers. In the practice of this embodiment, the pulp mat would generally be further subjected to fiberization by methods known in the art such as being fiberized by a hammermill to form the plurality of loose fibers to be entrained in the moving airsteam. The fibrous web material made by this alternative embodiment may further comprise treated or untreated synthetic fibers and/or super absorbent materials and/or additional treatments as was described above with reference to the previous embodiments.

Various additional potential processing and/or finishing steps known in the art such as aperturing, slitting, treating, or lamination of the fibrous web material with films or nonwoven web layers, may be performed without departing from the spirit and scope of the invention. Additionally, it will be apparent to those skilled in the art that other alterations or modifications may be made without departing from the spirit and scope of the present invention. It is therefore intended that all such modifications, alterations and other changes be encompassed by the claims. Numerous other patents have been referred to in the specification and to the extent there is any conflict or discrepancy between the teachings incorporated by reference and that of the present specification, the present specification shall control.

We claim:

1. A method for making a fibrous web comprising the steps of:
   a) providing a plurality of loose fibers;
   b) entraining the loose fibers in a stream of moving air;
   c) treating the fibers with an energy-activatable pre-polymer composition;
   d) subjecting the treated fibers to activation energy to initiate a cross-linking reaction in the energy-activatable pre-polymer composition; and
   e) collecting the fibers on a moving forming surface to form a fibrous web, either prior to the step of treating the fibers or after the step of subjecting the fibers to activation energy.

2. The method of claim 1 wherein the step of treating the fibers comprises spraying the energy-activatable pre-polymer composition into the stream of moving air while the fibers are therein entrained.

3. The method of claim 1 wherein the step of treating the fibers comprises spraying the energy-activatable pre-polymer composition onto the fibrous web after the step of collecting the fibers on the moving forming surface.

4. The method of claim 2 wherein the plurality of loose fibers comprises cellulosic fibers.

5. The method of claim 3 wherein the plurality of loose fibers comprises cellulosic fibers.

6. The method of claim 4 wherein the step of entraining the fibers in the stream of moving air further comprises entraining super absorbent material into the stream of moving air.

7. The method of claim 5 wherein the step of entraining the fibers in the stream of moving air further comprises entraining super absorbent material into the stream of moving air.

8. The method of claim 6 wherein the plurality of loose fibers further comprises from a positive amount to about 20 percent by weight of synthetic fibers.

9. The method of claim 7 wherein the plurality of loose fibers further comprises from a positive amount to about 20 percent by weight of synthetic fibers.

10. The method of claim 6 further comprising the step of compacting the web with pressure and wherein the cross-linking reaction initiated by the activation energy is substantially complete prior to the step of compacting the web.

11. The method of claim 6 further comprising the step of compacting the web with pressure and wherein the step of compacting the web is performed before the cross-linking reaction initiated by the activation energy is substantially complete.

12. The method of claim 2 wherein the energy-activatable pre-polymer composition comprises a photoinitiator and an epoxy resin.

13. The method of claim 3 wherein the energy-activatable pre-polymer composition comprises a photoinitiator and an epoxy resin.

14. The method of claim 12 wherein the energy-activatable pre-polymer composition further comprises a hydrophilic treatment.

15. A method for making a fibrous web comprising the steps of:
    a) providing a mat of fibers;
    b) treating the mat of fibers with an energy-activatable pre-polymer composition;
    c) forming a plurality of loose fibers from the treated mat of fibers;
    d) entraining the loose fibers in a stream of moving air;
    e) subjecting the fibers to activation energy to initiate a cross-linking reaction in the energy activatable pre-polymer composition; and
    f) collecting the fibers on a moving forming surface to form a fibrous web;
    wherein step f) may precede step e).

16. The method of claim 15 wherein the step of entraining the fibers in the stream of moving air further comprises entraining super absorbent material into the stream of moving air.

17. The method of claim 16 wherein the mat of fibers is a synthetic fiber mat.

18. The method of claim 16 wherein the mat of fibers is a cellulosic fiber mat and wherein the step of forming a plurality of loose fibers includes fiberizing the cellulosic fiber mat.

19. The method of claim 17 wherein the step of entraining the fibers in the stream of moving air further comprises entraining cellulosic fibers into the stream of moving air.

20. The method of claim 15 further comprising the step of compacting the web with pressure and wherein the cross-linking reaction initiated by the activation energy is substantially complete prior to the step of compacting the web.

21. The method of claim 15 further comprising the step of compacting the web with pressure and wherein the step of compacting the web is performed before the cross-linking reaction initiated by the activation energy is substantially complete.

22. The method of claim 16 wherein the energy-activatable pre-polymer composition comprises a photoinitiator and an epoxy resin.

* * * * *